(12) United States Patent
Caserta et al.

(10) Patent No.: US 7,530,503 B2
(45) Date of Patent: May 12, 2009

(54) DISPOSABLE DEVICE FOR DIFFUSION OF VOLATILE SUBSTANCES

(75) Inventors: Andrea Caserta, Barcelona (ES); Ruben Garcia Fábrega, Barcelona (ES); Jose Antonio Muñoz Martinez, Barcelona (ES); David Moreno Pérez, Barcelona (ES)

(73) Assignee: Zobele España, S.A., Barcelona (ES)

( * ) Notice: Subject to any disclaimer, the term of this patent is extended or adjusted under 35 U.S.C. 154(b) by 297 days.

(21) Appl. No.: 11/394,419

(22) Filed: Mar. 31, 2006

(65) Prior Publication Data

US 2007/0194368 A1  Aug. 23, 2007

(30) Foreign Application Priority Data

Feb. 23, 2006 (WO) ................ PCT/ES2006/000082

(51) Int. Cl.
 *A24F 25/00* (2006.01)
(52) U.S. Cl. .............................. 239/57; 239/34; 239/53; D23/368
(58) Field of Classification Search .................... 239/53, 239/55–59, 34; 206/0.5; D23/366, 368; 223/86, 89
See application file for complete search history.

(56) References Cited

U.S. PATENT DOCUMENTS 2,673,120 A * 3/1954 Bink et al. .................... 239/57
2,755,954 A * 7/1956 Antritter ...................... 239/57
5,115,976 A * 5/1992 Weiss et al. .................. 206/0.5
5,383,598 A * 1/1995 Styles ......................... 239/57
5,961,043 A * 10/1999 Samuelson et al. ............ 239/56

FOREIGN PATENT DOCUMENTS

| ES | 155540 | 2/1970 |
| ES | 2 019 539 | 3/1990 |

* cited by examiner

*Primary Examiner*—Steven J Ganey
(74) *Attorney, Agent, or Firm*—Knobbe Martens Olson & Bear LLP

(57) ABSTRACT

The device comprises a laminar element (1) made of a flexible material adapted to be folded along a folding line (26), comprising at least a first part (2) and a second part (4). Said first part (2) has a deposit (3) containing a product (30) origin of volatile substances. The second part (4) has a hook configuration (5) with a lateral opening (12) and a central groove (24) that can be occupied by removable adhesive means. Both parts (2, 4) are manufactured in a single industrial process, without additional parts but incorporating various attachment means and even other parts for functions of regulation or protection of the diffusion means, or which replicate the diffusion functionality allowing the user to combine effects. They also allow selecting the form of application in any location: hanging, adhered, joined to another identical device or folded and supporting itself on a horizontal surface.

18 Claims, 16 Drawing Sheets

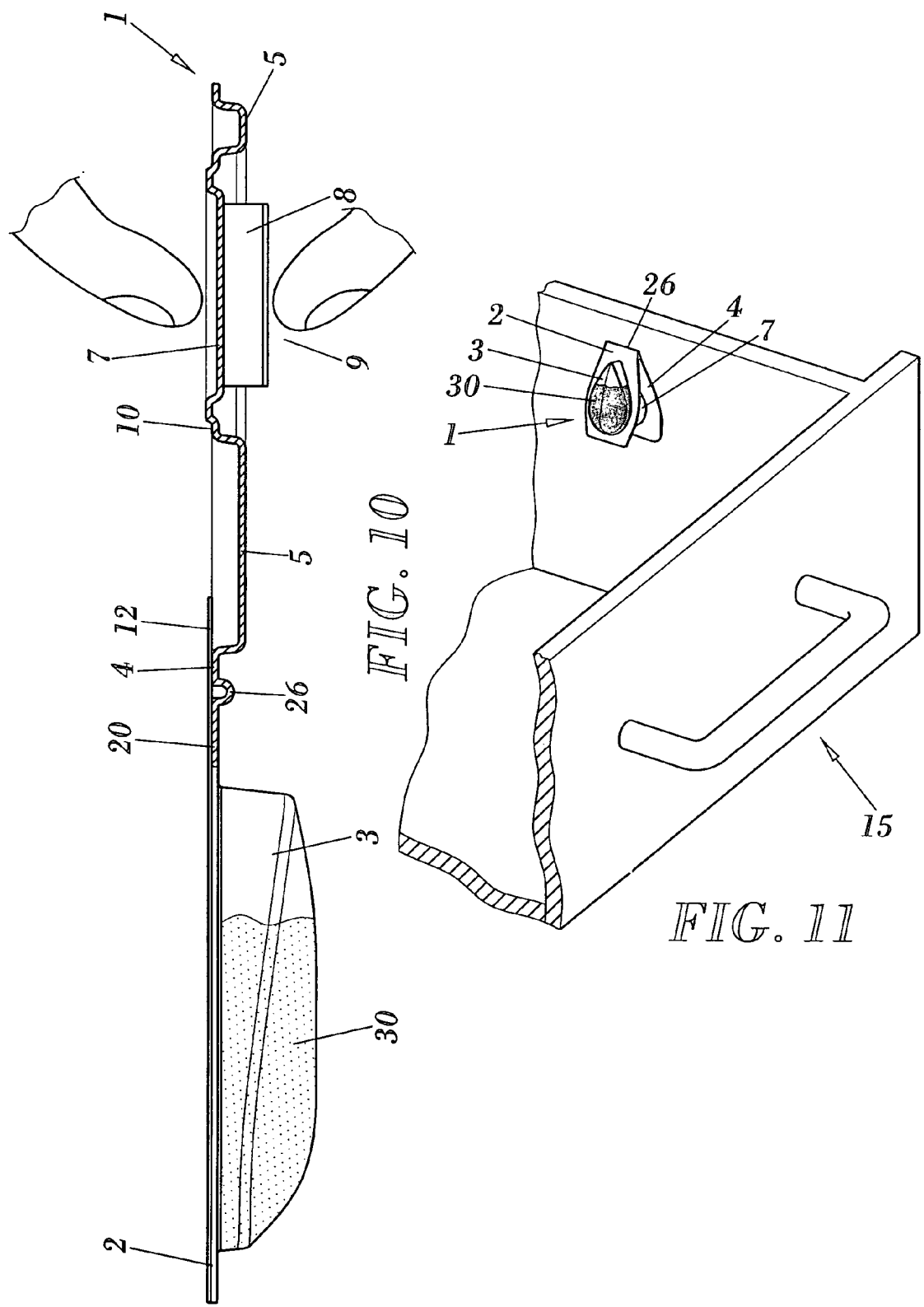

DISPOSABLE DEVICE FOR DIFFUSION OF VOLATILE SUBSTANCES

BACKGROUND OF THE INVENTION

1. Field of the Invention

The present invention is applicable in the industrial sector related to manufacturing devices for diffusing volatile substances obtained from a product in liquid, solid or powder form, particularly for diffusing fragrances, air disinfectants, insecticides, etc. in small spaces such as a car, a cupboard, a dishwasher, etc.

One object of the invention is to provide a diffuser of volatile substances with a construction having a minimal cost and maximum simplicity, with a design that is economical, simple and discreet, to constitute a disposable device with a great versatility of uses and/or applications.

Also an object of the invention is to provide the user with several alternatives to attach and/or use the device in a specific location, allowing to hang it, glue it or stand it in the chosen place, or even to join it to another identical device to combine it with another diffuser of the same or different substance, according to the wish of the consumer, by integrating various attachment means in the same device and its structure, conferring a great versatility of use to the diffuser while making it easy to use by the end user.

2. Description of the Related Art

Diffusers are well known for air fresheners, insecticides, deodorants etc., usually in liquid form or dispensed as a gel or tablets which, by the appropriate evaporation means, distribute the active particles of the compound in the air.

To contain such compounds in the diffuser devices the market provides a great variety of containers, generally made of plastic, their design often depending on the most common destination which the device has been made for.

Specifically, when the diffuser is to be used in small enclosed spaces, such as a cupboard or a car, containers of the type incorporating a hook are known to be very useful to hang the device at a suitable place in said spaces.

In this line of containers for air fresheners and the like, particularly those of a low cost, there are many examples which include a hook that allows hanging the diffuser at the most convenient location. As an example of a container with a hook holding deodorising and/or insecticide tables, Spanish Utility Model ES 0155540 U can be mentioned, while for the case of air freshening liquids or gels, the hanging container of Spanish Patent ES 2019539 may be cited.

The hanging nature of these diffusion devices generally does not increase the cost of production of the product from the manufacturer's point of view, and therefore does not increase the cost to the end user. In most cases these are disposable diffusers which the user can easily dispose of when the effect of the chemical substance contained in them runs out.

The constructive characteristics of the containers for volatile substances mentioned above constrain the consumer to use the container only in locations where it is possible to hang it safely, as they are specifically meant to be used in this way.

But in addition to hanging these containers in the desired area the user may also wish to place the diffuser in other ways in order to increase its effect, depending on the place in which it will be used, which may not always include a suitable point from which to hang the device containing the air freshening or disinfectant compound or substance.

For this reason, it is desirable that the container of the diffuser have means that allow several forms of placing the device without increasing the cost of the device or complicating the structure of the diffuser.

SUMMARY OF THE INVENTION

The present invention solves the drawbacks described above among others, in each and every aspect described in the background section.

The invention disclosed herein relates to a disposable device for diffusing active substances that comprises a laminar element formed by at least a first and a second part, between which is preferably defined a fold area of the flexible laminar element common to both of the aforementioned parts, which favours bending the device for its subsequent positioning on a flat surface in an inverted V shape. Preferably, said laminar element is made of a flexible and low cost material, such as cardboard or plastic, its parts being configured according to various alternative embodiments as described below.

Incorporated in said first part of the laminar element is a deposit containing a product that provides the volatile substances, including a diffusion area for said volatile substances. This deposit is obtained by conforming a cavity in the first part of said laminar element with the desired design, such as a water drop shape, the same industrial method being used to manufacture the device with any shape of the deposit, or simply requiring to change a removable part of the shaping mould used on the laminar device.

Configured in the second part of the laminar element is a hook having a lateral opening meant to receive an object that the user can insert until it reaches another central opening or groove of the hook, so that the device can be hung from said object at will.

A first embodiment consists of incorporating in the second part of the laminar element, at its upper end, a retractable top flap free to swivel about a hinge or hinge line between a non-retracted position in which the lateral opening of the hook is open and a retracted position in which the top flap closes the lateral opening of the hook, so that if the user hangs the device from this hook the retracted top flap secures this hooking, reducing the risk that the diffuser device may accidentally be caused to fall from its position.

In another embodiment of the invention, the first part of the laminar element is prolonged on its lower end as a third part that can also pivot about a corresponding hinge line between a non-retracted position in which the area of diffusion of volatile substances is completely open and a retracted position in which the area of diffusion is at least partly covered by the third part. Thus, said third part can be used to protect the area of diffusion of the volatile product, or to help control the evaporation of said product.

The evaporable product or volatile formula, as mentioned above, is contained in the deposit located in the first part of the laminar element, inside a housing provided for this purpose, preferably a bubble or recess containing the liquid with the required air freshener, insecticide or disinfectant in the amount needed to allow its evaporation through the diffusion area. Therefore, a membrane is provided over the area that completely covers the mouth of the recess, retaining the liquid in it while allowing the diffusion of volatile substances when the area is not covered by a third part as described. Incorporated in the evaporation membrane is a sealing or water-soluble protective film, generally made of disposable materials (plastic, aluminium, paper) that the consumer must remove to expose to the air the membrane and therefore the area from which the volatile substances are diffused.

Regardless of the manner chosen by the user to place the device, hanging, glued as explained further below, or standing on a horizontal surface, the evaporation membrane is not in contact with the surface on which it is placed, thus preventing its undesired impregnation with the substances. However, after the diffuser sealing film is removed a person may inadvertently touch the membrane (such as a child attracted by the smell of the product), which may leave some substance on his/her finger with the danger that it may reach the mouth.

To further protect the diffusion area the third part is designed with an area having orifices or perforations to allow air circulation which, in the retracted position of said third part, coincides with the aforementioned diffusion area of the first part. In addition, the second part has lateral tabs which, when the third part is retracted, engage the end opposite to the hinge so that the third part is clipped onto the second part, its perforated area covering the evaporation membrane and thereby preventing it from being touched. To improve the lateral air flow, the third part includes lateral air ducts which, even when the diffusion area is covered by said membrane, contributes to the evaporation of the product as air will flow through these ducts and orifices provided in this protective system that makes it impossible to touch the membrane from the outside.

Another configuration of the third part in which it acts as a regulation system is that, as said third part can pivot about the hinge provided on the bottom end of the first part, the third part of the laminar element can bend toward the diffusion area in the first part to form an angle of varying size that determines a greater or lesser diffusion of the volatile substances. For example, the third part can be turned from a position coplanar to the aforementioned other two parts of the laminar element as much as 180°, to a position above the diffusion area, in which position said third part will cover the membrane and thereby hinder the evaporation of the product. To achieve a greater rate of diffusion the third part can be separated further from the evaporation membrane by a certain angle, allowing air to pass and thereby regulating the amount of fragrance emitted by the diffuser at the user's will.

In addition, the first part can have at least two lateral flaps, also free to pivot about corresponding lateral hinges, similarly allowing to control lateral air flow. Opening the lateral flaps of said first part and the third part towards the diffusion area of the first part allows constituting an approximately closed duct for air circulation vertically only, thereby regulating the evaporation of the volatile liquids contained in the deposit.

A last example of configuration of the third part as a regulation element for diffusion includes in said part, made of a flexible material, several creases by which the user can fold said third part one or more times. After pivoting it as described above, folding the third part at the various creases allows uncovering the diffusion area by sectors and therefore varying the membrane surface exposed to air through which the evaporation actually occurs by this simple regulation method (single, double, triple etc. according to the number of creases established in the third part of the device).

Other embodiments of the device relate to other means of attachment or coupling integrated in the device to give the user greater options of use or positioning, in addition to hanging the diffuser from an object using the hook configured in the second part.

A first option is standing the flexible laminar element on a horizontal surface by simply bending it slightly in half at a crease provided between its first and second parts, so that the two parts define an angle that allows the device to stand alone on the surface in a fully functional manner, the membrane being separated from said surface and ready to allow the diffusion of the substances as the air flows freely or regulated by the system described above, between the two supporting parts.

Also, after folding the device at said central line to form a convenient angle between the parts the user may decide to hang it, not directly from the hook but instead resting by its centre on the edge of an object such as a bin, a shoe or wherever the user fancies The flexibility of the material from which the laminar element or device body is manufactured allows conceiving other embodiments that allow hooking or coupling this diffuser to another of the same characteristics. One embodiment consists of placing the first and second parts with their corresponding grooves opposite each other, so that when the laminar element is bent thereby bringing its two parts closer to one another one groove can be made to meet the other and engage it, closing the device as if in a ring. The user can then decide to hang the device from a tubular object by embracing it and clipping the first part on the second.

It is also possible to select another diffuser with the same grooves and couple the two by joining their respective first parts with the grooves provided in them and similarly engaging the second parts with their grooves. This process can be extended to form rings of two or more similar diffusers, which means that the user can multiply the amount or intensity of aromatic substance that can be released at the location of the ring of diffusers, or incorporate devices with different products to combine fragrances or the effect desired by the user.

To give the user another option for joining two identical devices, another embodiment of the invention involves duplicating the two parts described hitherto for the laminar element. Thus, the first part is extended at the bottom into a fourth part that can pivot about a hinge line provided on its bottom end; in turn, this fourth part is extended at the bottom to form a fifth part, with all parts sharing the laminar element, giving the latter part a hook-like configuration opposite to the position of the hook of the second part. This embodiment therefore has two hooks which, due to the flexibility of the material from which the device is made, can be brought close to each other by the user until they engage one another. Again, and as the fourth part can include a container with another volatile product, this determines a ring with two diffusers, with two formulations that may be different in order to obtain a combined effect. In addition, the ring is defined so that it protects the diffusion area in its interior, further hindering access to the membrane by a child or other person. The device thus conformed with the two hooks engaging each other can for example be placed on wider wardrobe bars.

Another option for the user when placing the diffuser device described herein is provided by including means in the second part of the laminar element, which is configured in a hook shape, for attachment by adherence.

More specifically, this last embodiment of the invention disclosed consists of determining in the second part a weakened line that internally defines a laminar portion occupied by the inside of the hook. This weakened line can be perforated on the laminar element or be provided with suitably spaced notches that allow detaching the laminar portion from the rest. The attachment means by adherence, which can be a paper or padded element impregnated with glue or another adhesive, a magnetic element or small magnet, or Velcro® type male and female pieces are incorporated on one surface of the laminar portion delimited by said weakened line. The device can thus be attached to many surfaces, such as adhered to a wooden door, fixed by a magnet on a refrigerator door, attached to a car dashboard, inside a drawer, etc.

The user can simply press the laminar portion on one or both faces with a finger to detach it partially or fully from the second part of the laminar element, as determined by the weakened line, which can be open or closed, sufficiently to leave free the end of the hook and connect its lateral opening to the central groove of the hook by which the device can be easily hung anywhere, such as from a car rear-view mirror, a coat hanger or many other commonplace objects. Once it is hung, combining the first implementation of the device with this last one, the lateral opening of the hook may be closed with the upper flap of the second part of the laminar element to improve the attachment to the object.

In short, the laminar element conforming the device the construction of which is described is valid for several applications, by integrating the various attachment means adapted to allow hanging the device anywhere, alone or engaged to another, standing it on a horizontal surface, or adhering it on the location and in the position most convenient to the user.

The construction of the diffuser device object of the invention is very simple, as all the parts are manufactured in a single industrial process without requiring additional parts. Moreover, as complex thermoplastic films may be used to obtain by heat forming the laminar device used to constitute the device, diffusers, containers or systems can be made that are heat resistant (up to 80° C.), or water-soluble systems that are activated by contact with water, etc. Additionally, the flexible laminar element that constitutes the base of said device is made of transparent plastic, allowing the user to view the content and determine how much is left of the product that provides the volatile substances. Thus, when this product is exhausted the consumer may discard the diffuser or container described.

The flexible material sheet conforming the body of a single piece can be perforated, forming the various parts including the described hook, hinges and/or weakened line, by a special ribbing that enhances the mechanical properties of the assembly.

BRIEF DESCRIPTION OF THE DRAWINGS

To complete the description being made and in order to aid a better understanding of the characteristics of the invention, according to a preferred embodiment thereof, a set of drawings is accompanied forming an integral part of the description where, for purposes of illustration and in a non-limiting sense the following is show:

FIG. 10 shows a cross section view of the upper sector of the invention revealing on the side the portion with the adhesive means detachable from the body that constitutes the diffuser device, according to one possible embodiment.

FIG. 11 shows a perspective view of the device in one application option, folded and glued inside a drawer.

DETAILED DESCRIPTION OF THE PREFERRED EMBODIMENT

Figure 1:
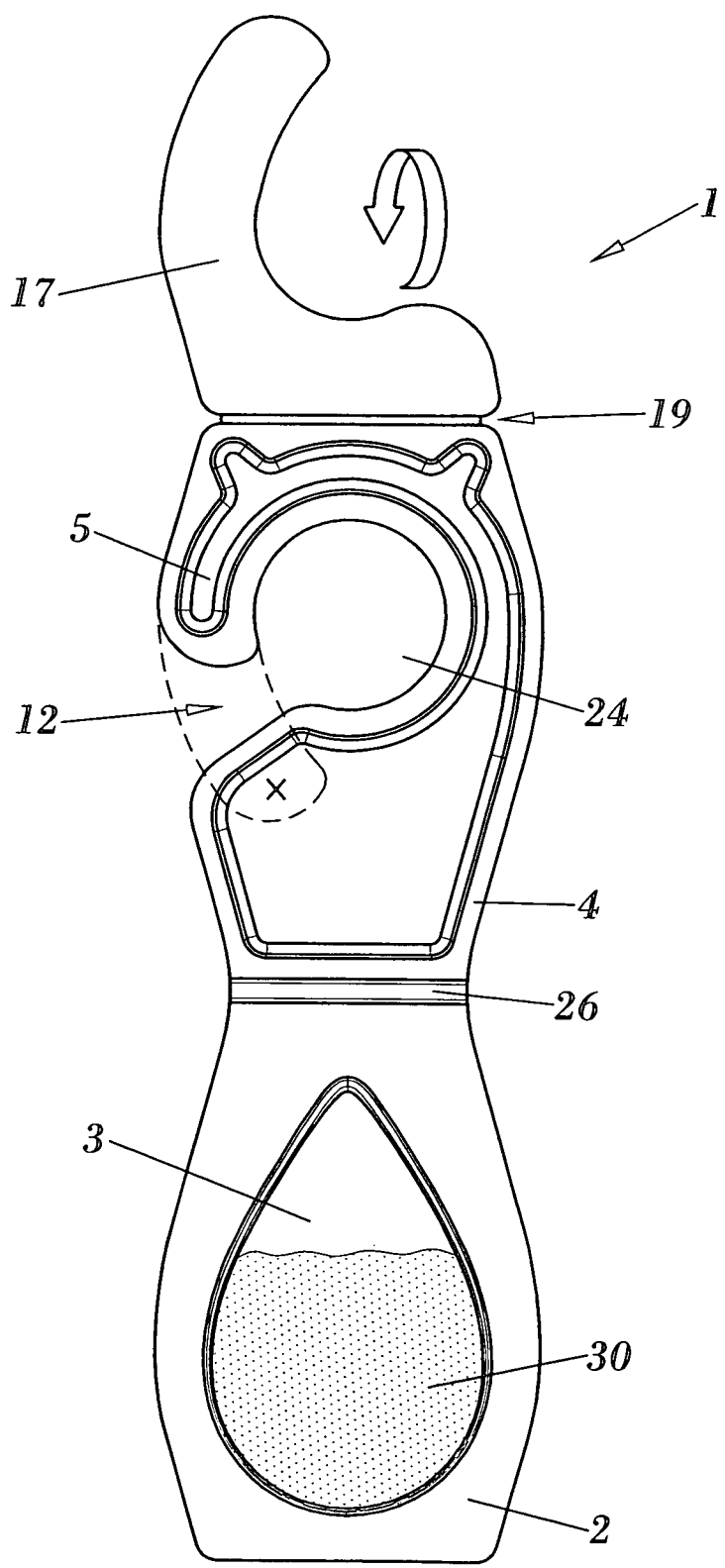
FIG. 1 shows a front view of the diffuser device for volatile substances according to a preferred embodiment with a top flap to close the hook.

In view of FIG. 1, a possible embodiment of the invention can be described as a disposable device for diffusing volatile substances constituted from a laminar element (1) of heat formed plastic that comprises at lest a first part (2) and a second part (4), with a deposit (3) in said first part (2) that contains a product (30), establishing on its rear surface a diffusion area (25) of the volatile substances produced by evaporation of the product (30). In the second part (4) the laminar element (1) has a hook (5) configuration with a lateral opening (12) and a central groove (24), normally communicated with each other.

In this specific embodiment represented in FIG. 1, the second part (4) has a top flap (17) that can pivot 180° about a hinge (19) provided on its upper end, between a non-retracted position in which said lateral opening (12) is open and a retracted position in which said upper flap (6) closes the lateral opening (12) of the hook (5). Optionally, to secure the closure, the flap (17) can have adhesive or other means on the end farthest from the second part in order to attach it to said part after the user hangs the device and pivots the flap (17) by 180° until placing said end next to the second part, thereby closing the lateral opening (12) as shown in FIG. 1.

Figure 2A:
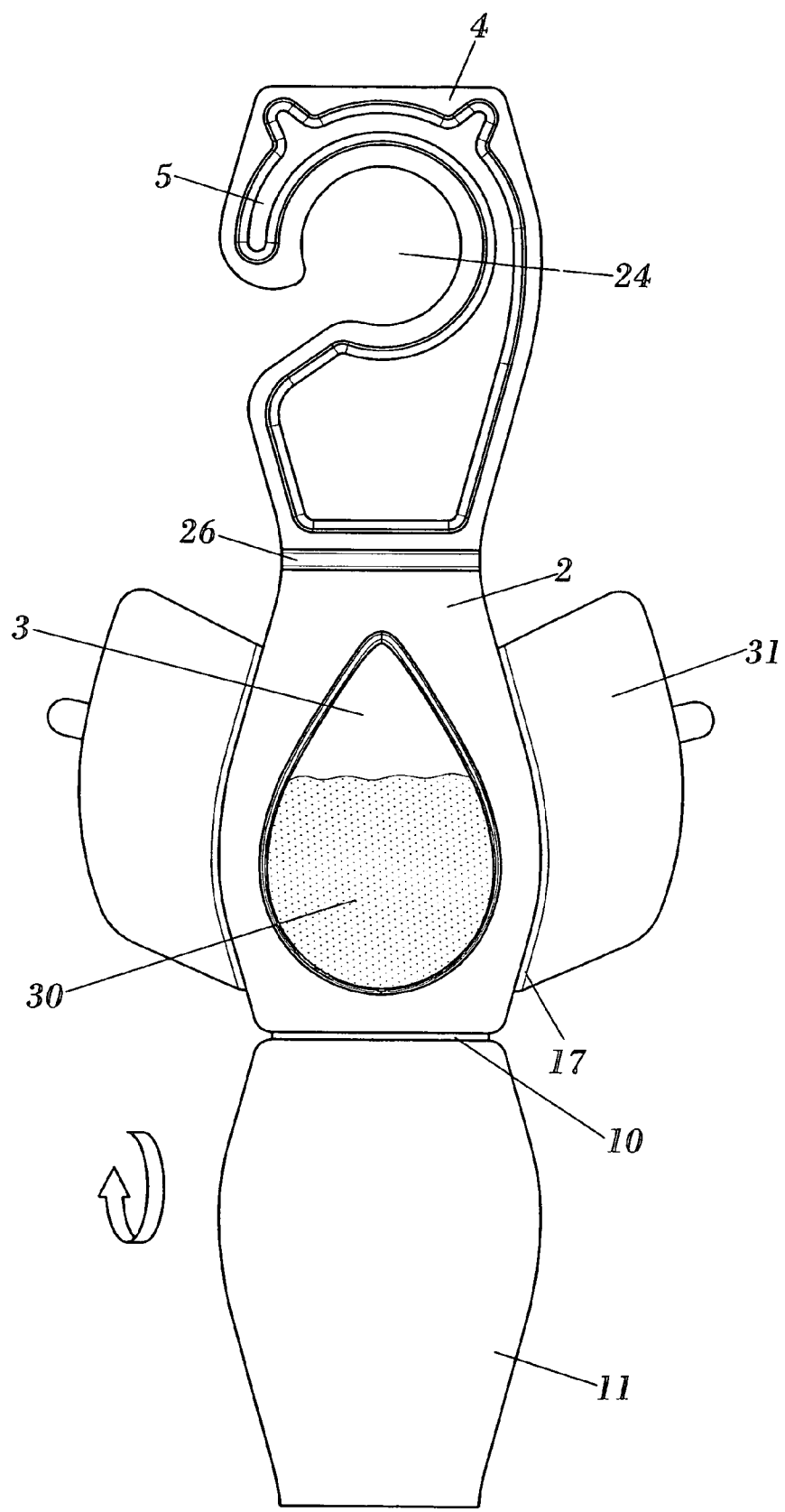
FIG. 2 shows front and side views of the diffuser device according to another embodiment of the invention with a part for regulating the diffusion of the substances and lateral flaps to complete said function.
Figure 2B:
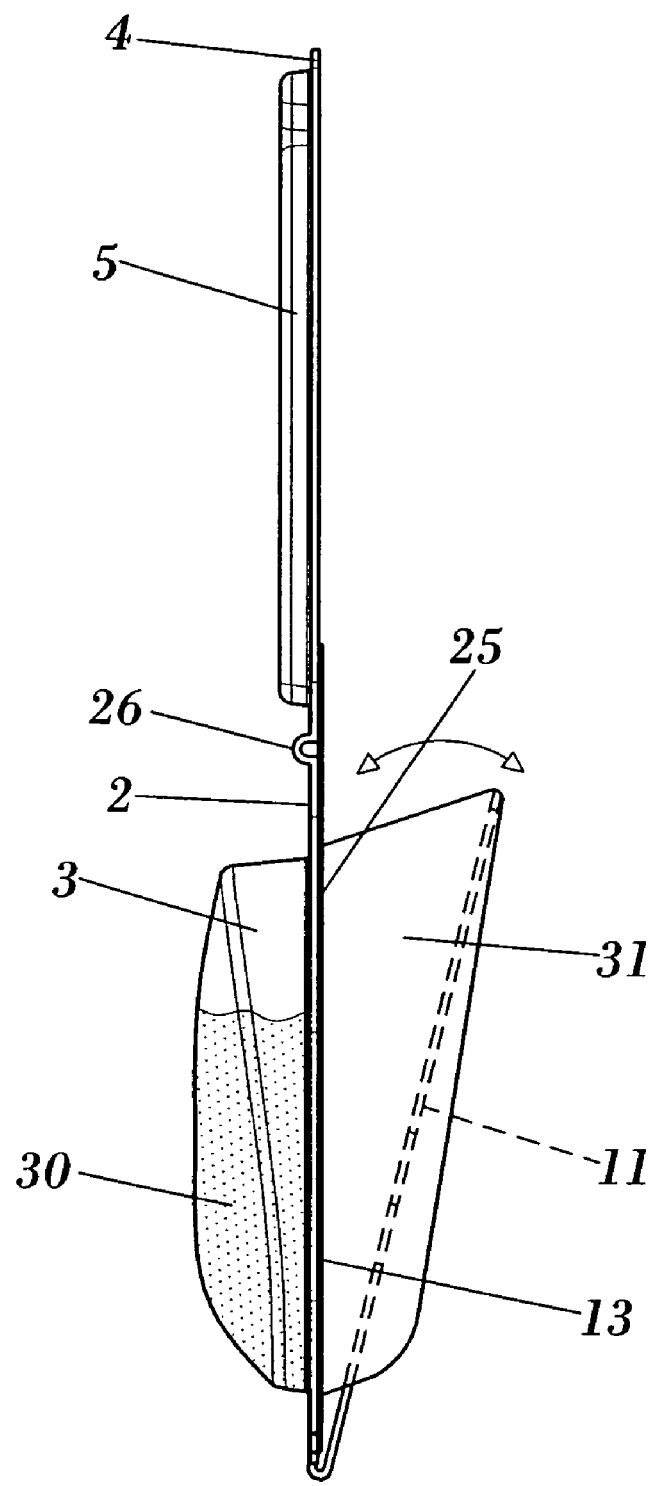

FIG. 2 shows other possible embodiments of the invention, wherein the first part (2) is extended on the bottom as a third part (11) that can pivot about a hinge (10) provided on the bottom end of said first part (2) between a retracted position, until reaching an angle (X) with the first part (2) adjustable by the user in which said third part (11) covers at least partially said diffusion area (25) and a non-retracted position in which the diffusion area (25) is completely uncovered by the third part (11), as shown in inset B of FIG. 2. Optionally, the first part (2) has at least two lateral flaps (31) that can pivot about corresponding hinges (17) provided on the sides of said first part (2).

Figure 3A:
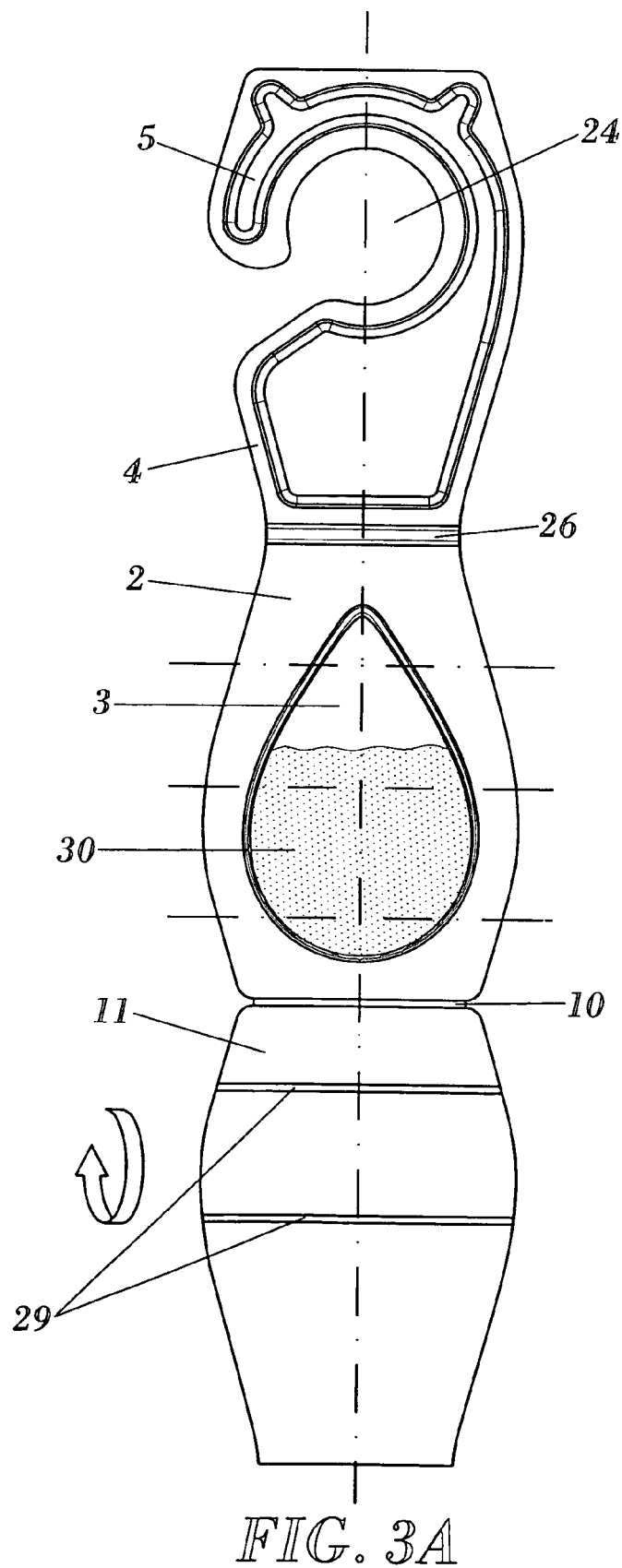
FIG. 3 shows front and side views of the device, according to another embodiment of the invention, with a triple system for regulating substance diffusion.
Figure 3B:
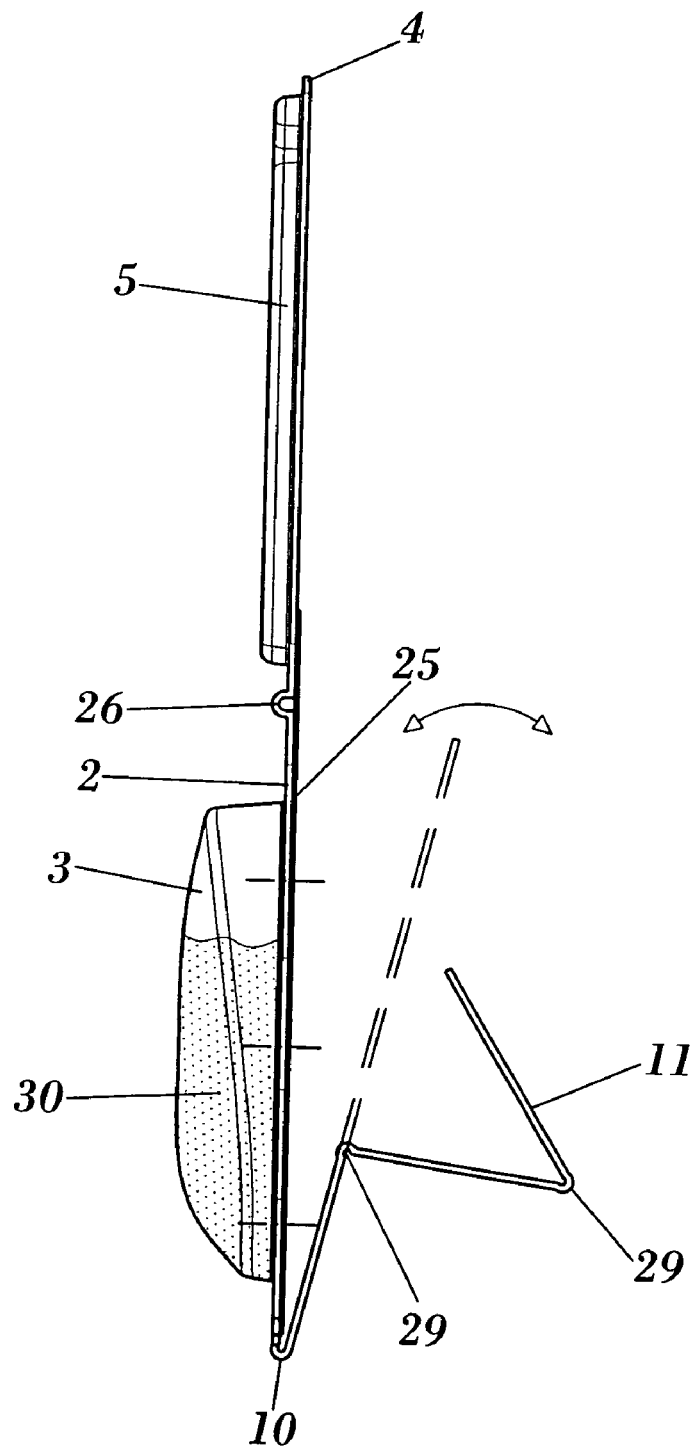

FIG. 3 illustrates a similar regulation system having a flexible third part (11) but including a folding line (29), so that in its retracted position said third part (11) can be folded at will by the user, as shown in inset B of FIG. 3, to partially uncover the diffusion area (25).

Figure 4A:
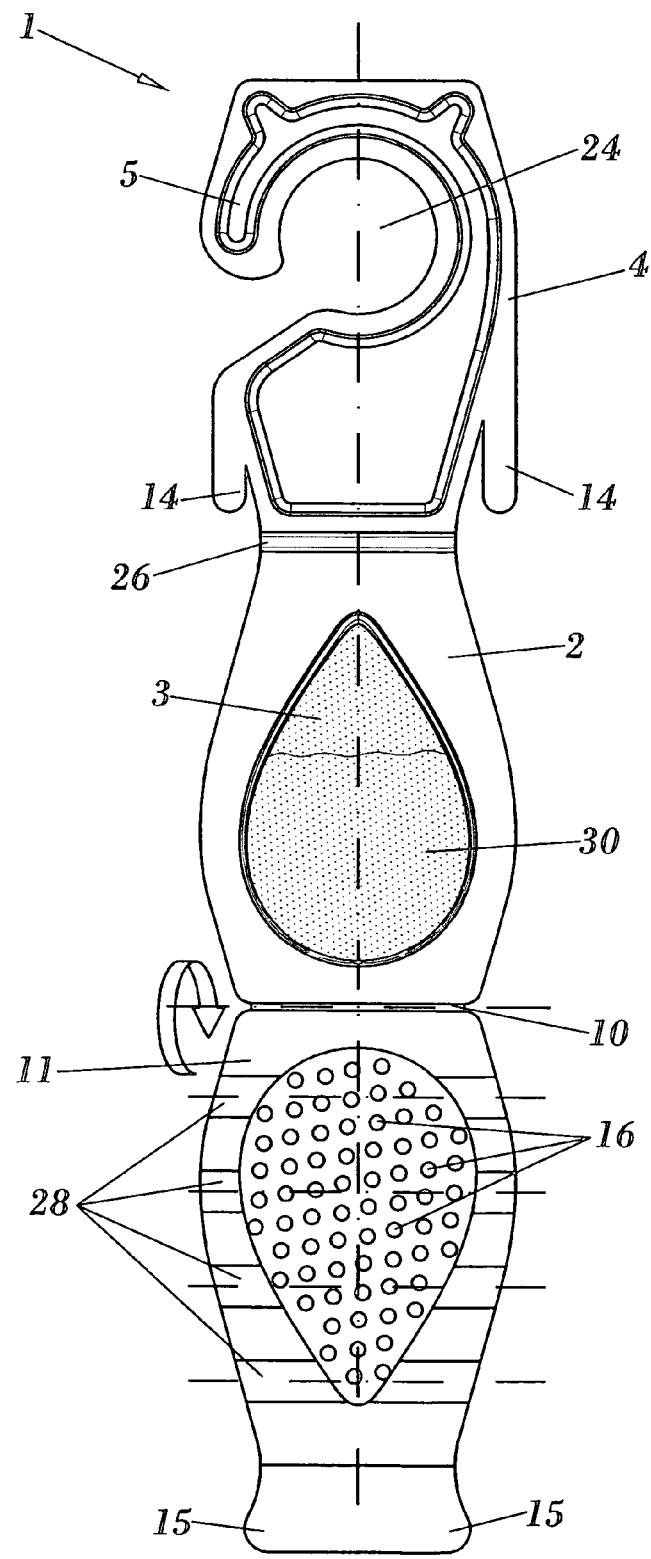
FIG. 4 shows front and side views of the device object of the invention, according to another possible embodiment with a part protecting the evaporation membrane.
Figures 4B, 4C:
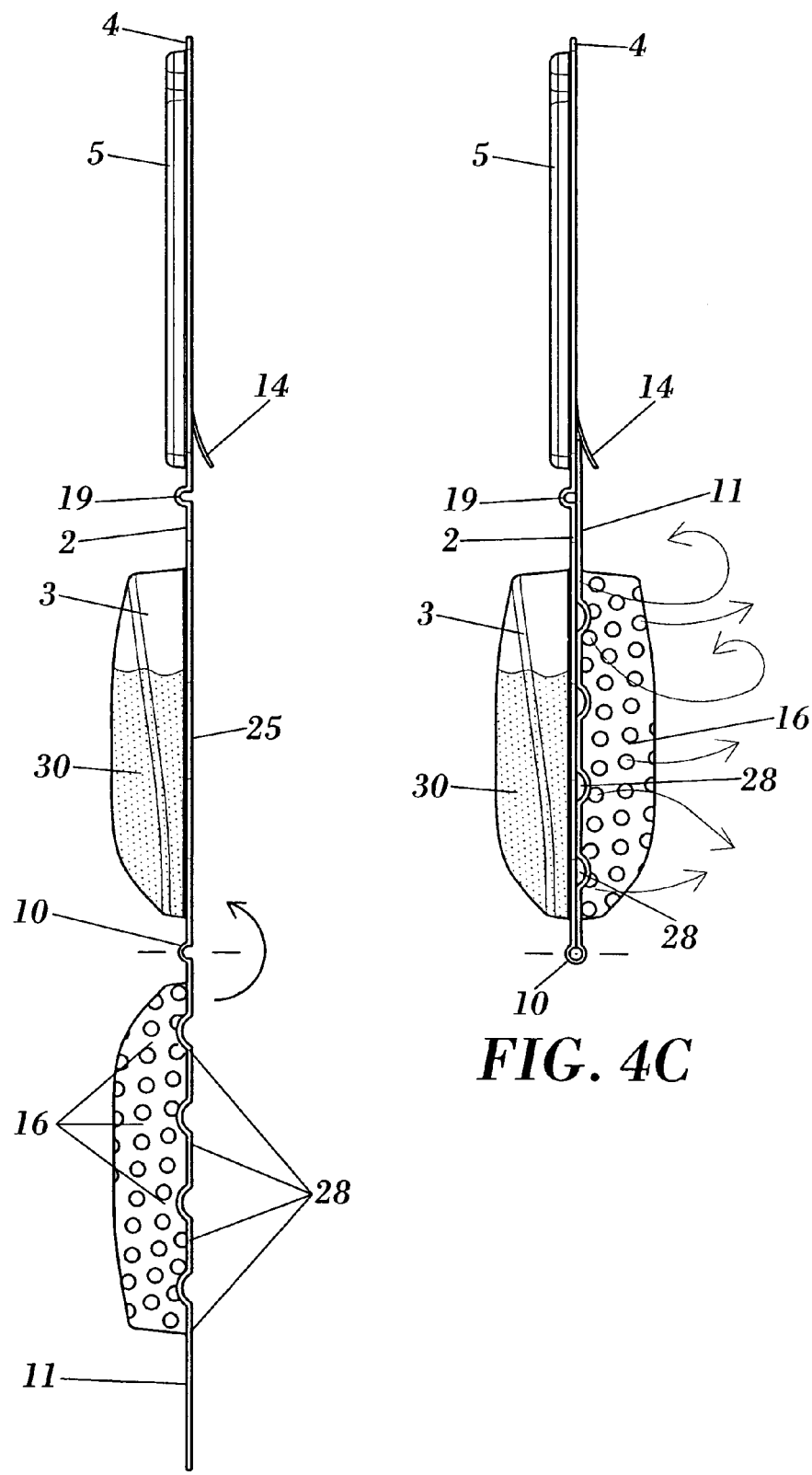

FIG. 4 shows the third part (11) adapted as a protector for the diffusion area (25), having an area with orifices (16) and lateral ducts (28) for air inlet/outlet. In the retracted position of the third part (11), its area with orifices (16) coincides with the diffusion area (25). The second part (4) incorporates two lateral tabs (14) on which the lower end (15) of the third part (11) engages, this is, the end opposite that of pivoting about the hinge (10). As represented in inset B of FIG. 4, the lateral tabs (14) are extracted by separating them slightly from the second part (4) of the laminar element (1) and the protective third part (11) pivots 180° about the rear part of the first part (2), covering the diffusion area (15) as shown in inset C.

Figure 5A:
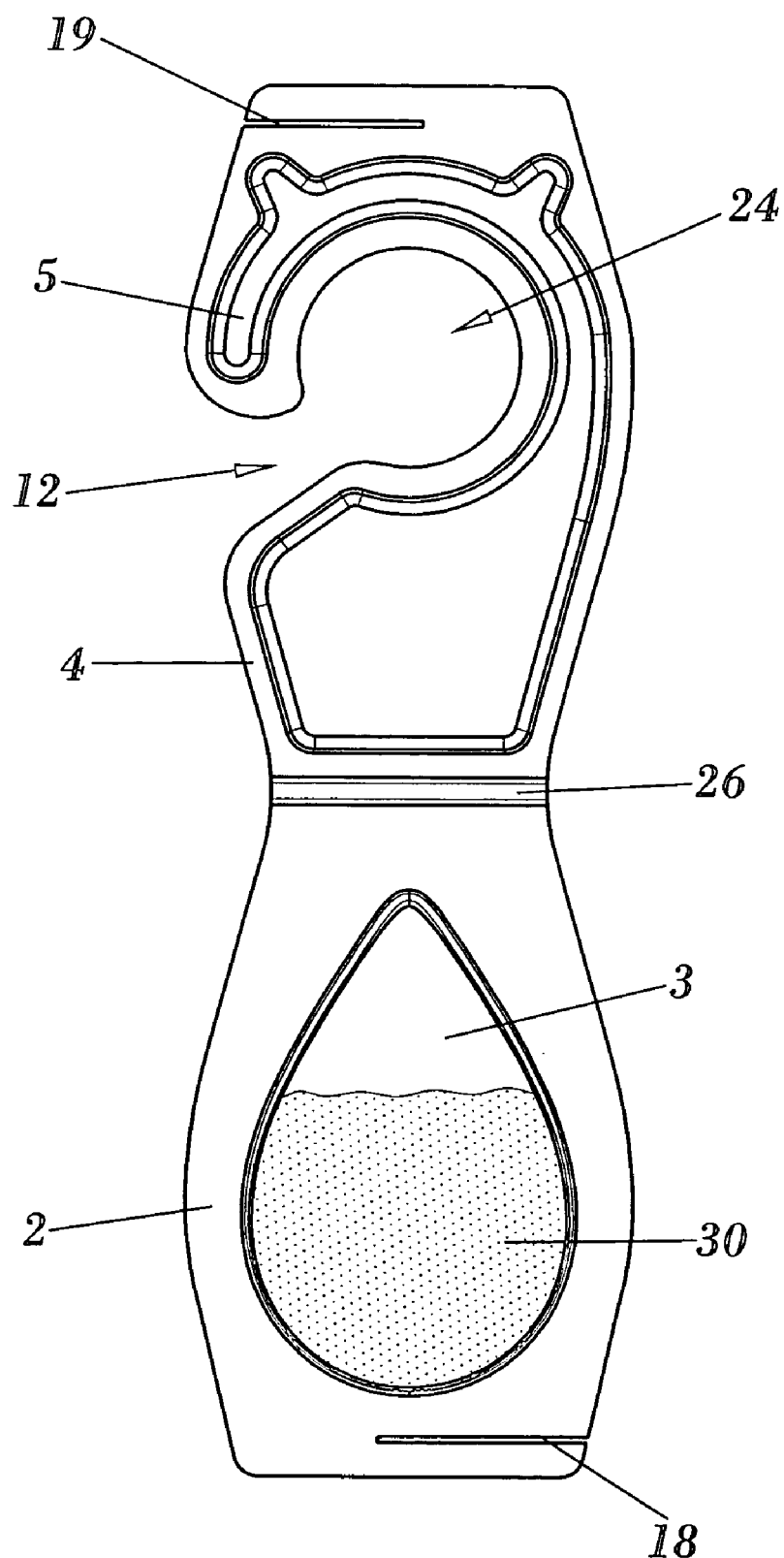
FIG. 5 shows a front view of the device object of the invention, according to another embodiment with engagement grooves.
Figure 5B:
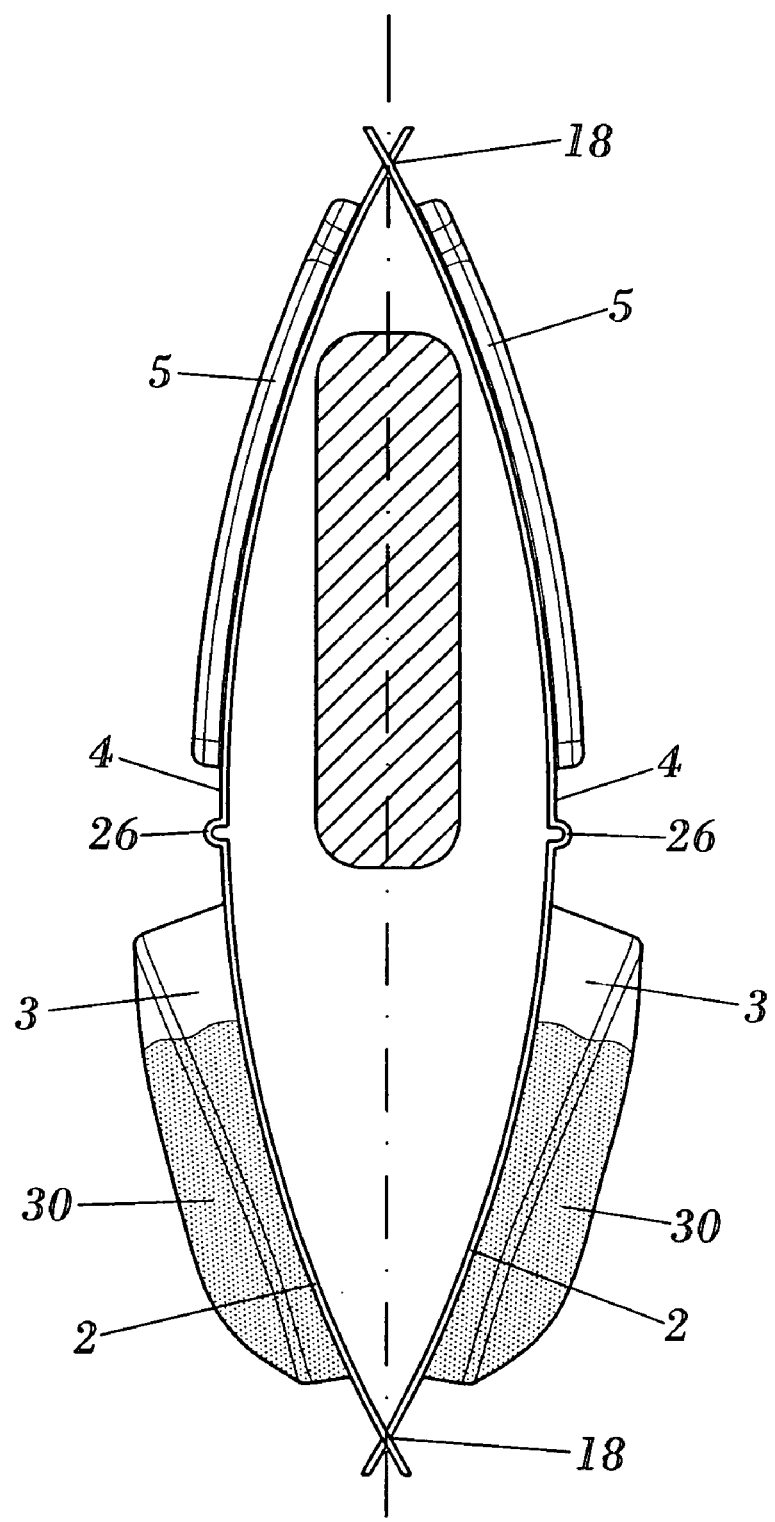
Figure 6A:
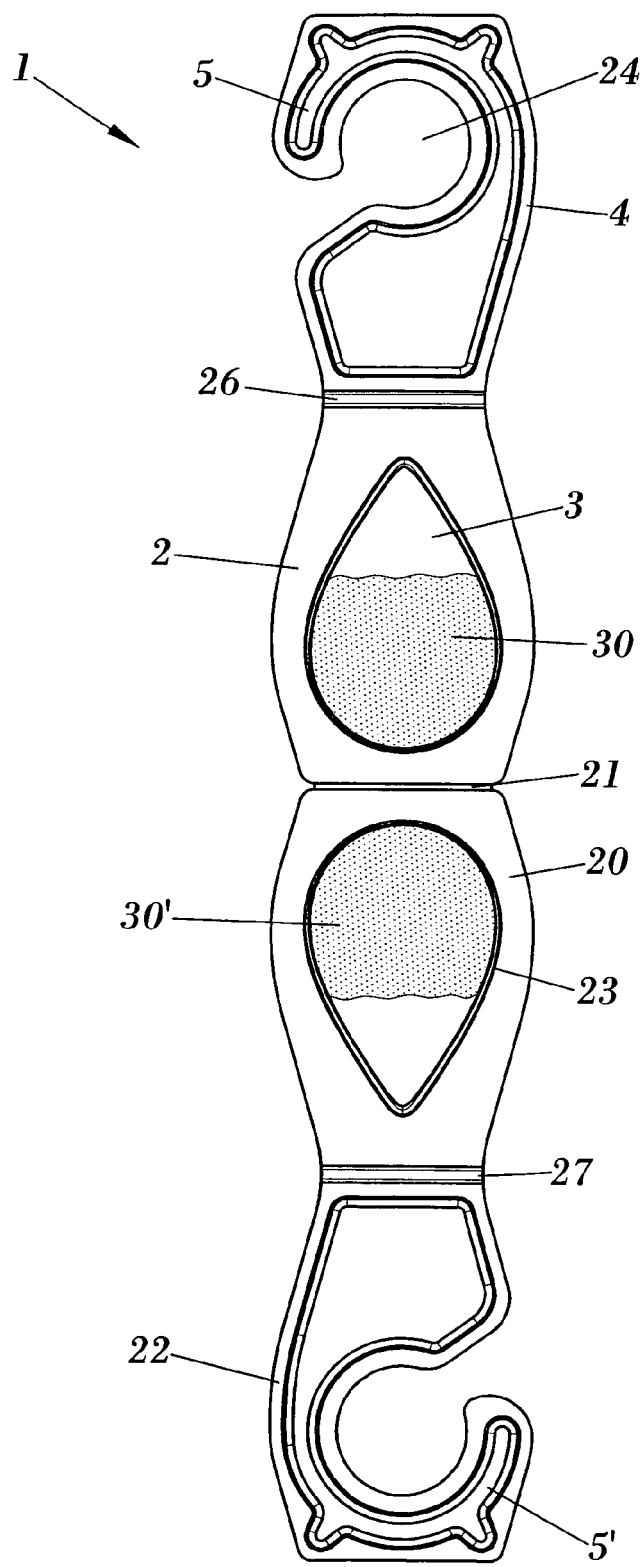
FIG. 6 shows a front view of the device object of the invention, according to another possible preferred embodiment with a double hook.
Figure 6B:
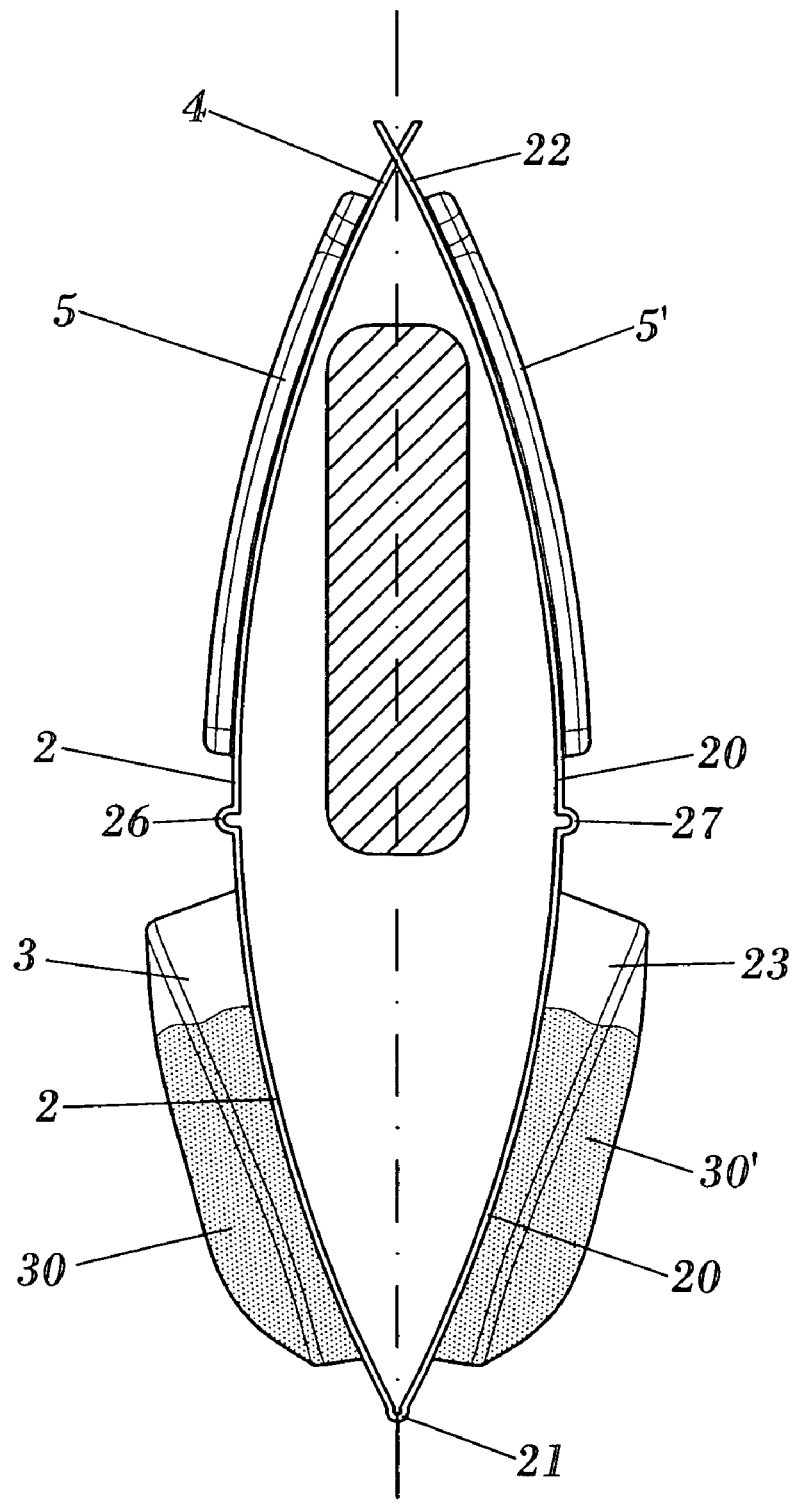

If the user wishes to use two volatile liquid diffusers together, several alternative embodiments of the invention are proposed. According to that represented in FIG. 5, the first part (2) and second part (4) respectively incorporate grooves (18, 19) that are adapted to engage corresponding grooves provided on the first and second part of a similar second disposable device for volatile substances, which is disposed with its grooves opposite said grooves (18, 19) as shown in inset B.

According to another embodiment in which the first part (2) of the laminar element (1) is prolonged on the bottom as a fourth part (20) that can pivot about a hinge (21) provided on the bottom of said first part (2), the fourth part (20) extended as a fifth part (22) provided with a hook (5') configuration, said fourth part (20) and fifth part (22) sharing said laminar element (1). The fourth part (20) has a container (23) for a product (30') that provides volatile substances. The assembly conforms a double diffuser device for volatile substances that can adopt a ring shape for hanging it, by joining the hooks (5, 5') opposite each other, as shown in inset B.

In the aforementioned figures of the flexible laminar element (1) a central folding line (26) is defined between the first part (2) and the second part (4), as well as another central folding line (26) between the fourth part (20) and the fifth part (22), along which the user can fold said laminar element (1).

Figure 7:
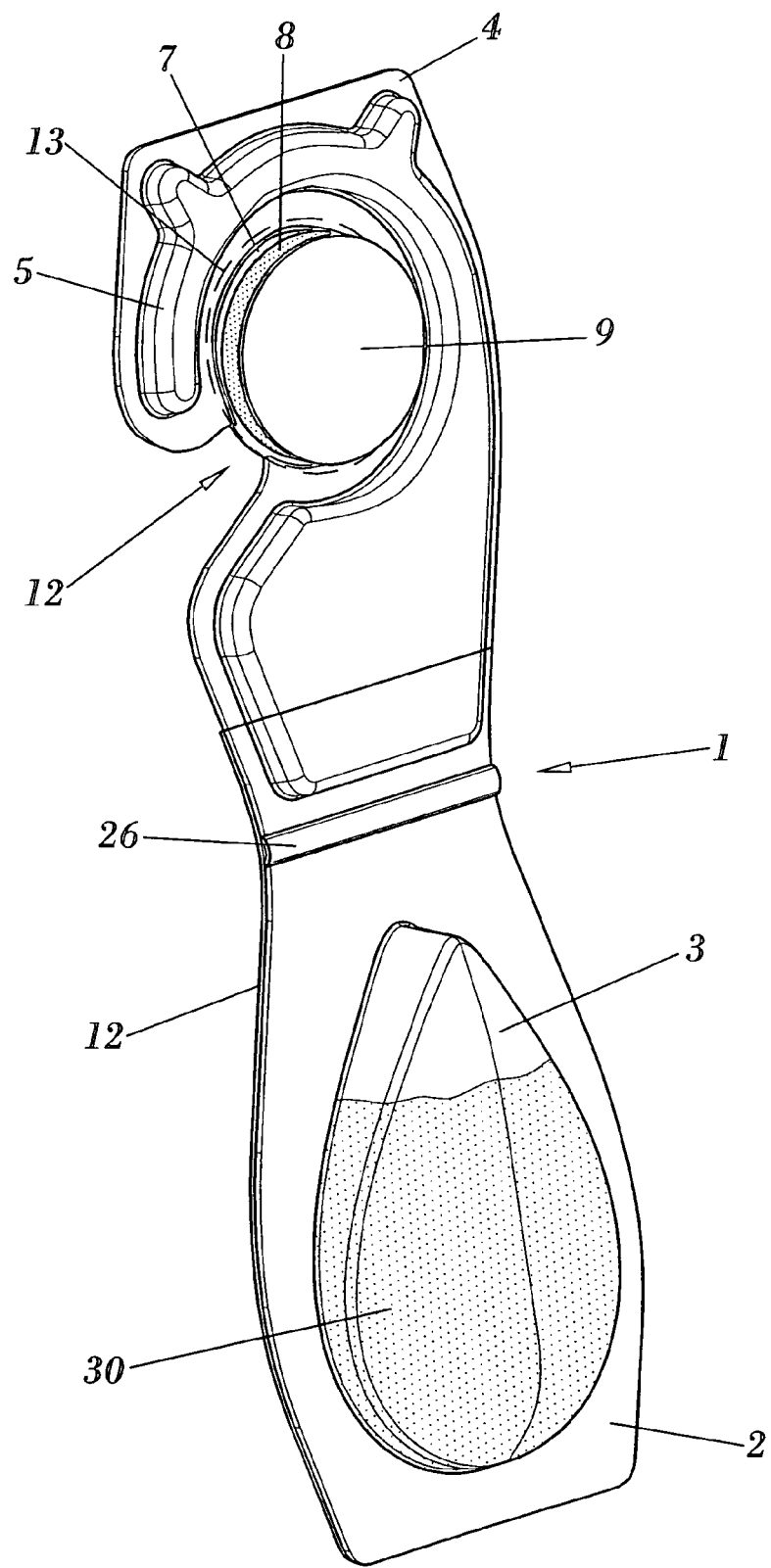
FIG. 7 shows a perspective view of the device object of the invention, according to a preferred embodiment incorporating means for attachment by adherence.

The second part (4) of the laminar element (1) represented in FIG. 7 incorporates means for attachment by adherence that preferably consist of a foam pad (8) glued on one surface to a laminar portion (7), also heat formed in plastic, constituting a closed, normally circular surface placed on the inside of the hook (5), occupying the space defined for the central groove (24). On the opposite surface, the pad (8) is impregnated with adhesive and covered with a protective film (9) of paraffin paper, both the pad (8) and the film (9) being adapted in shape and size to the laminar portion (7) determined inside the hook (5) conformed as a single part in the second part (4). This double layer adhesion means also prevents the device from contacting any object, as the pad (8) separates it sufficiently from the surface on which it is glued.

Figure 8:
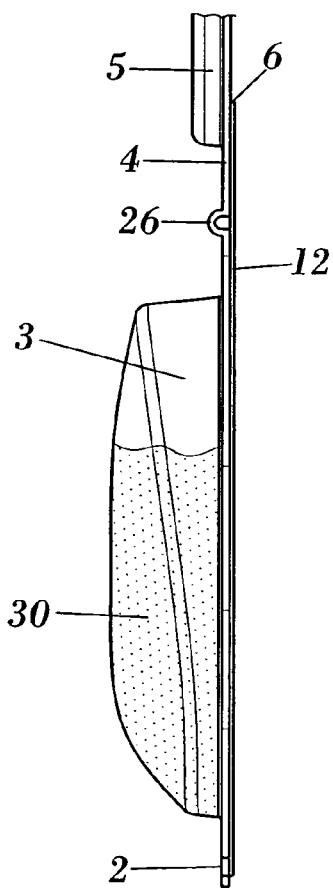
FIG. 8 shows an elevation view of the first part of the device, showing in detail the evaporation membrane and the protective layer covering the diffusion area, according to the embodiment represented in the previous figure.

The first part (2) has, for example, an approximately oval or drop-like shape and at its centre is the deposit (3), circular or with a suitable shape appealing to the end user, which contains the product (30) formulated to release the perfume or other suitable volatile substance. As appreciated in FIG. 8, the rear surface of the deposit (3) is covered by an evaporation membrane (6) that seals it retaining the product (30) and covers the diffusion area (25) through which the product (30) begins to evaporate when the user removes a protective and sealing layer (12), such as an aluminium foil that covers entirely or in part the first part (2) of the laminar element (1).

Figure 9:
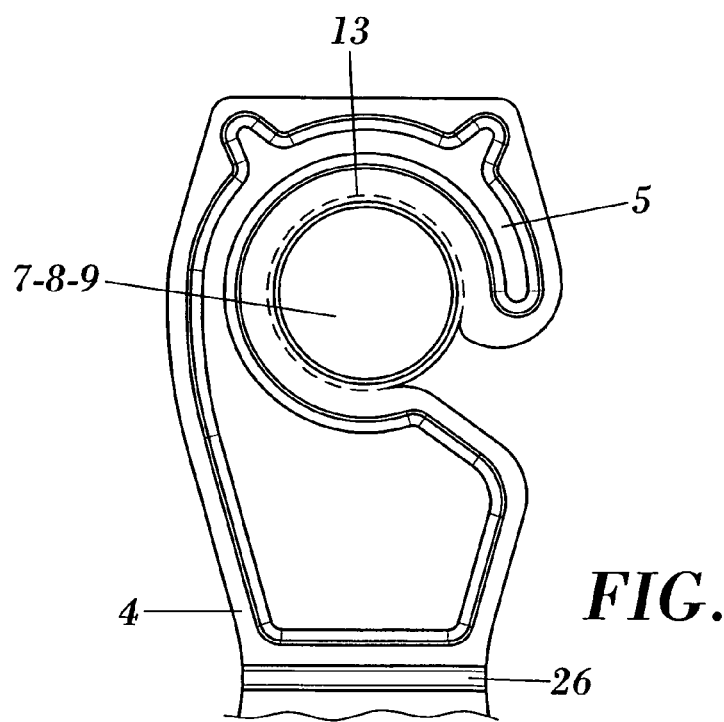
FIG. 9 shows a back view of the second part of the device, according to the embodiment represented in FIG. 7.

The rear surface of the second part (4), shown in FIG. 9, has a weakened line (13) that internally delimits the laminar portion (7) on which the means for attachment by adherence are disposed on one surface. The two surfaces of said laminar portion (7) constitute a surface that can be easily detached from the laminar element (1), simply by the user pressing with a finger (14) on such surface of the laminar portion (7), which for greater comfort is slightly recessed with respect to the outline defined by the inside of the hook (5), as shown in detail in FIG. 10.

Figure 14:
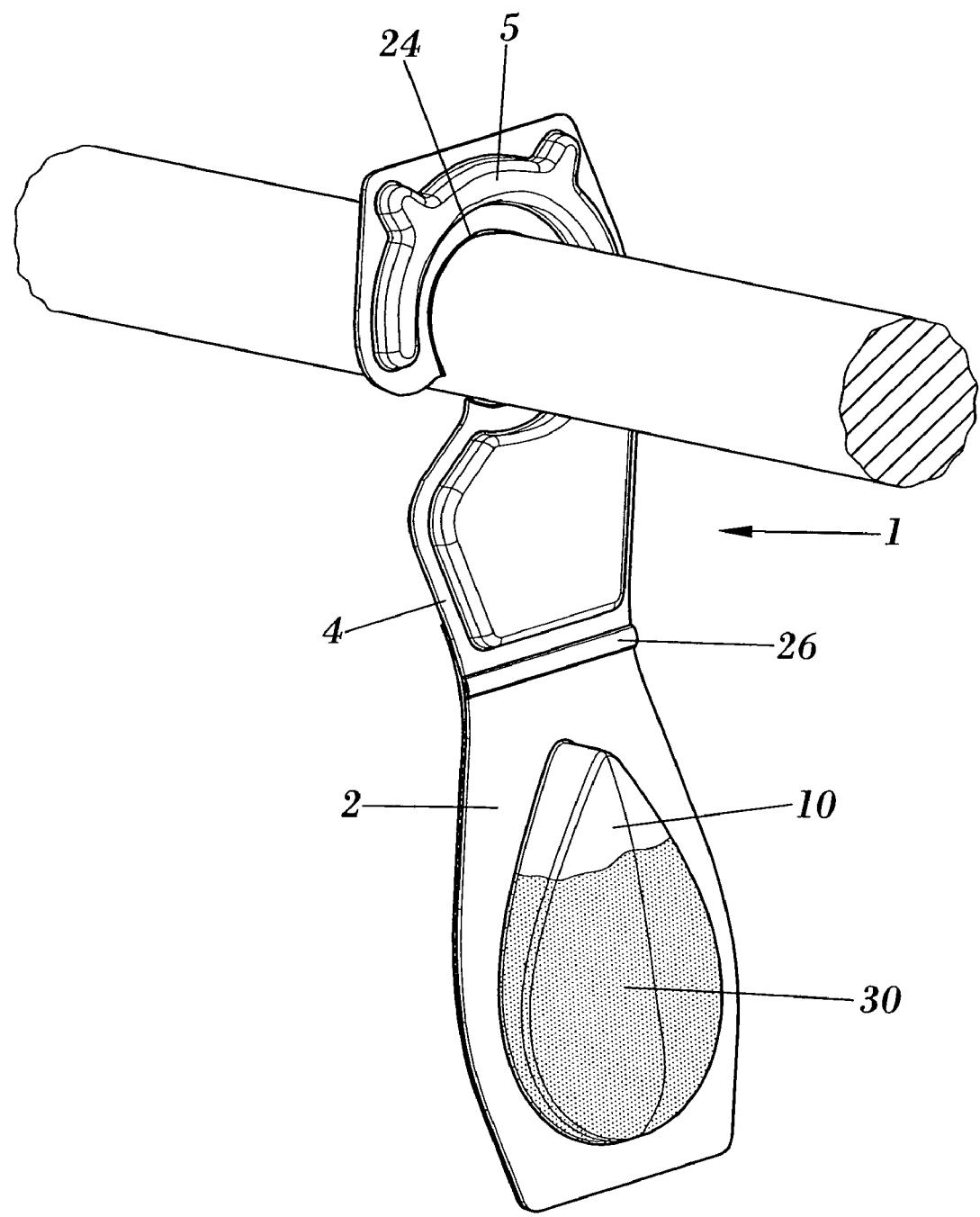
FIG. 14 shows a perspective view of the diffuser in a last but no less important application option, without being folded and hanging from its hook, both inside cupboards and from car parts such as the rear support of a rear-view mirror, turn signal levers, etc.

The weakened line (13) can be perforated, as shown in FIG. 9, or provided with a plurality of notches (10) that weaken the union between the laminar portion (7) and the hook (5), so that a slight pressure with a finger, as represented in FIG. 10, on said laminar portion (7) will separate it from the second part (4) and the inside of its hook (5) will be left empty, leaving the central groove (24) ready to allow hanging the device object of the invention, as shown in FIG. 14.

Figure 12:
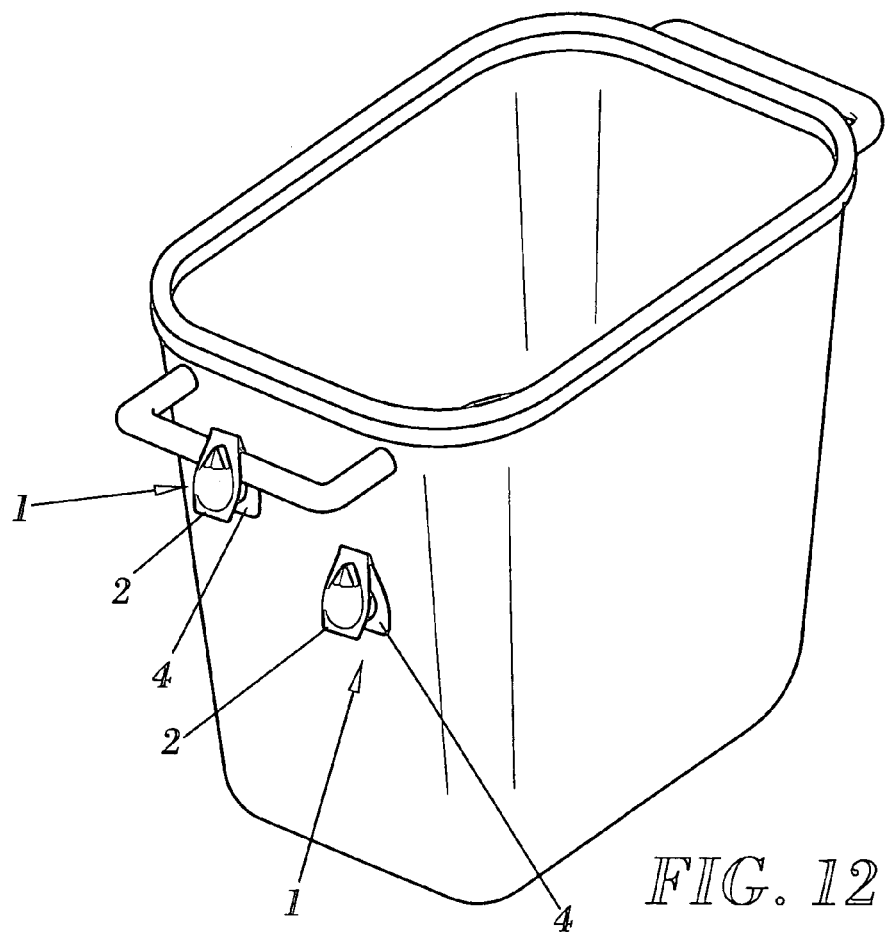
FIG. 12 shows a perspective view of the diffuser in another application option, folded and hung from the outer edge of a bin or glued inside it.
Figure 13:
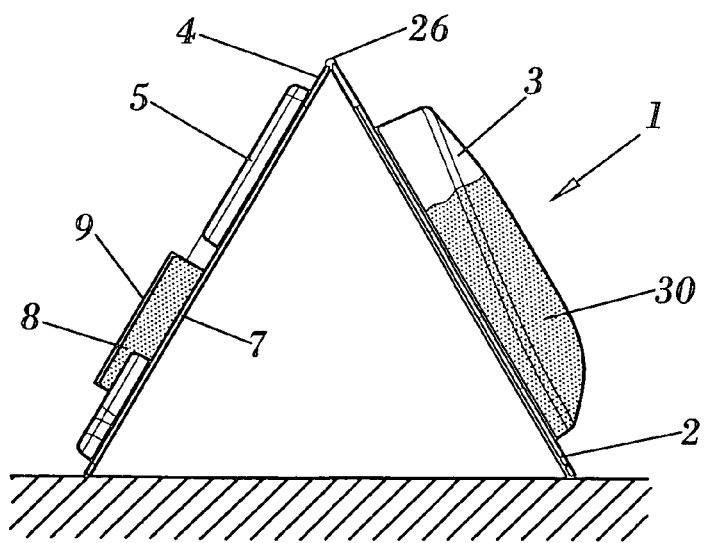
FIG. 13 shows a perspective view of the diffuser in another application option, folded and standing unassisted on a horizontal surface.

Aside from using the adhesive means proposed for attaching it to a surface, such as an internal face of a drawer or the outer surface of a bin, as shown in FIGS. 11 and 12, the user may fold the laminar element (1) by the folding line (26) defined between the first part (2) and the second part (4), forming a suitable angle (X) that allows standing it on any flat surface, as shown in FIG. 13. The device of the invention can also be attached to an object by folding the laminar element (1) in half in order to hang it directly from the folding line (26), instead of from the hook (5) provided for this purpose, using a suitable element of the object such as those shown in FIG. 12, the mouth or handles of a rubbish bin or wastebasket.

These are some of the possible uses and embodiments of the diffuser object of the invention, which show the versatility of this device, with a simple structure made entirely from very low cost and disposable materials.

What is claimed is:

1. Disposable device for diffusing volatile substances, comprising:
   a laminar element with at least a first part and a second part,
   in said first part, a deposit containing a product origin of the volatile substances having a diffusion area of said volatile substances, and
   in said second part a hook configuration with a lateral opening,
   wherein the second part has a top flap that can pivot about a hinge provided on the upper end of said second part between a non-retracted position in which the lateral opening is open and a retracted position in which said top flap closes the lateral opening of the hook.

2. Disposable device for diffusing volatile substances, comprising:
   a laminar element with at least a first part and a second part,
   in said first part, a deposit containing a product origin of the volatile substances having a diffusion area of said volatile substances, and
   in said second part a hook configuration with a lateral opening,
   wherein the first part is extended on the bottom as a third part that can pivot about a hinge provided on the lower end of said first part, between a non-retracted position in which the diffusion area is completely uncovered and a retracted position in which the third part covers at least partially said diffusion area;
   wherein the second part has two lateral tabs and in that the third part has an area with orifices which, in its retracted position, coincides with the diffusion area and, in said retracted position, the end of the third part opposite the hinge engages the lateral tabs; and
   wherein the third part has lateral air ducts.

3. Disposable device for diffusing volatile substances, according to claim 2, wherein the first part has at least two lateral flaps that can pivot about corresponding hinges provided on the sides of said first part.

4. Disposable device for diffusing volatile substances, according to claim 2, wherein the third part is made of a flexible material and has at least one folding line, so that said third part, in its retracted position, can be folded at the user's will to partially uncover the diffusion area.

5. Disposable device for diffusing volatile substances, comprising:
 a laminar element that has at least a first part and a second part,
 in said first part, a deposit containing a product origin of the volatile substances and with a diffusion area of said volatile substances, and
 in said second part a hook configuration with a lateral opening,
 wherein the second part has a weakened line that internally defines a laminar portion, which incorporates on one side attachment means by adherence and on the other side determines a surface that can be detached from the laminar element when exerting a force with a finger, opening a central groove that communicates with the lateral opening of the hook adapted to hanging the device.

6. Disposable device for diffusing volatile substances, according to claim 5, wherein the weakened line is perforated.

7. Disposable device for diffusing volatile substances, according to claim 5, wherein the weakened line is weakened by a plurality of notches that constitute a fragile union between the hook and the laminar portion.

8. Disposable device for diffusing volatile substances, according to claim 5, wherein the means of attachment by adherence consist of a pad impregnated with adhesive and covered by a protective film, both the pad and the film being adapted in size and shape to the laminar portion.

9. Disposable device for diffusing volatile substances, according to claim 5, wherein the means of attachment by adherence consist of a male piece provided on one face with a plurality of hooks and a female piece provided on one face with a plurality of loops adapted so that the hooks of the male piece are engaged inside them, both pieces having an adhesive face by which one piece is attached to the laminar portion of the device and the other piece is attached to a surface selected for attaching the device by said means of attachment by adherence.

10. Disposable device for diffusing volatile substances, according to claim 9, wherein the means of attachment by adherence are of Velcro ®.

11. Disposable device for diffusing volatile substances, according to claim 5, wherein the means of attachment by adherence consist of a magnetic element joined to the laminar portion.

12. Disposable device for diffusing volatile substances, according to claim 5, wherein the laminar element is made of a flexible material.

13. Disposable device for diffusing volatile substances, comprising:
 a laminar element of a flexible material that has at least a first part and a second part,
 in said first part, a deposit containing a product origin of the volatile substances and with a diffusion area of said volatile substances, and
 in said second part a hook configuration with a lateral opening,
 wherein the first part is extended on the bottom as a fourth part that can pivot about a hinge provided on the bottom end of said first part, said fourth part extending on its bottom as a fifth part provided with a hook configuration, said fourth part and fifth part sharing the flexible laminar element;
 wherein the laminar element can be bent by a central folding line defined between the fourth part and the fifth part; and
 wherein the hook has mechanical reinforcement ribs configured in the laminar element.

14. Disposable device for diffusing volatile substances, according to claim 13, wherein the fourth part has a container of a product origin of volatile substances.

15. Disposable device for diffusing volatile substances, according to claim 13, wherein the laminar element can be bent by a central folding line defined between the first part and the second part.

16. Disposable device for diffusing volatile substances, according to claim 13, wherein the laminar element comprises at least a wide area and a narrow area, establishing the central folding line in the narrow area.

17. Disposable device for diffusing volatile substances, according to claim 13, wherein the diffusion area is covered by a membrane that can diffuse the volatile substances of the product.

18. Disposable device for diffusing volatile substances, according to claim 17, wherein it comprises a protective and sealing layer that covers the membrane and prevents the evaporation of the product.

* * * * *